United States Patent
Zimring et al.

(10) Patent No.: US 10,274,480 B2
(45) Date of Patent: Apr. 30, 2019

(54) STEAP3 AS A BIOCHEMICAL MARKER OF RED BLOOD CELL STORAGE AND TOXICITY

(71) Applicant: Bloodworks, Seattle, WA (US)

(72) Inventors: James Charles Zimring, Seattle, WA (US); Karen S. de Wolski, New Haven, CT (US)

(73) Assignee: Bloodworks, Seattle, WA (US)

(*) Notice: Subject to any disclaimer, the term of this patent is extended or adjusted under 35 U.S.C. 154(b) by 77 days.

(21) Appl. No.: 15/308,836

(22) PCT Filed: May 6, 2015

(86) PCT No.: PCT/US2015/029552
§ 371 (c)(1),
(2) Date: Nov. 3, 2016

(87) PCT Pub. No.: WO2015/171826
PCT Pub. Date: Nov. 12, 2015

(65) Prior Publication Data
US 2017/0276665 A1    Sep. 28, 2017

Related U.S. Application Data

(60) Provisional application No. 61/989,440, filed on May 6, 2014.

(51) Int. Cl.
*G01N 33/53* (2006.01)
*G01N 33/80* (2006.01)
(Continued)

(52) U.S. Cl.
CPC ....... *G01N 33/5005* (2013.01); *C12Q 1/6883* (2013.01); *G01N 33/53* (2013.01); *G01N 33/80* (2013.01); *C12Q 2600/106* (2013.01); *C12Q 2600/156* (2013.01); *C12Q 2600/158* (2013.01); *G01N 33/48* (2013.01);
(Continued)

(58) Field of Classification Search
CPC .... G01N 33/5005; G01N 33/53; G01N 33/80; G01N 33/48; G01N 2333/82; G01N 2333/90209; G01N 2800/7066; C12Q 1/6883; C12Q 2600/106; C12Q 2600/156; C12Q 2600/26; C12Q 2600/158
See application file for complete search history.

(56) References Cited

U.S. PATENT DOCUMENTS

2014/0178904 A1    6/2014    Zimring

FOREIGN PATENT DOCUMENTS

| WO | WO 2014/036183 A2 | 3/2014 |
| WO | WO2014036183 A2 | 3/2014 |

OTHER PUBLICATIONS

Grandchamp et al. A novel type of congenital hypochromic anemia associated with a nonsense mutation in the STEAP3/TSAP6 gene. Blood 118 (25): 6660-6666 (Dec. 15, 2011).*

(Continued)

*Primary Examiner* — Gailene Gabel
(74) *Attorney, Agent, or Firm* — Bloodworks; C. Rachal Winger; Thu Nguyen

(57) ABSTRACT

Compositions and methods for determining post-transfusion survival or toxicity of red blood cells and the suitability of red blood cell units for transfusion by measuring the levels of one or more markers in a red blood cell sample are provided.

12 Claims, 2 Drawing Sheets

Specification includes a Sequence Listing.

(51) Int. Cl.
  *C12Q 1/6883* (2018.01)
  *G01N 33/50* (2006.01)
  *G01N 33/48* (2006.01)
(52) U.S. Cl.
  CPC ............... *G01N 2333/82* (2013.01); *G01N 2333/90209* (2013.01); *G01N 2800/7066* (2013.01)

(56) References Cited

OTHER PUBLICATIONS

Ohgami et al. STEAP proteins are metalloreductases. Blood 108 (4): 1388-1394 (Aug. 2006).*
Accession No. BC095421, *Homo sapiens* STEAP family member 3, mRNA 7-9 (cDNA clone MGC:110951 Image:30336214), complete cds, Mar. 19, 2007 [online] Accessed on Aug. 18, 2015 <http://www.ncbi.nlm.nih.gov/nuccore/BC095421>, 4 pages.
Gilson, et al., "A novel mouse model of red blood cell storage and post transfusion in vivo survival," Transfusion, vol. 49, No. 8, 2009, pp. 1546-1553.
Hess, "Red cell storage," J. Proteomics, vol. 73, No. 3, 2010, pp. 368-373.
Hod, et al., "Transfusion of human volunteers with older, stored red blood cells produces extravascular hemolysis and circulating non-transferrin-bound iron," Blood, vol. 118, No. 25, 2011, pp. 6675-6682.
Kor, et al., "Red blood cell storage lesion," Bosn. J. Basic Med. Sci., vol. 9 Suppl 1, 2009, pp. 21-27.
Lambe, et al., "Identification of a Steap3 endosomal targeting motif essential for normal iron metabolism," Blood, vol. 113, No. 8, 2009, pp. 1805-1808.
Accession No. NM_001085409, Mus musculus STEAP family member 3 (Steap3), transcript variant 1, mRNA <https://www.ncbi.nlm.nih.gov/nuccore/146134511/>, 5 pages, (2002).
Accession No. NP_001078878, metalloreductase STEAP3 [Mus musculus] <https://www.ncbi.nlm.nih.gov/protein/146134512/>, 4 pages, (1996).
Ohgami, et al., The Steap proteins are metalloreductases, Blood, vol. 108, No. 4, 2006, pp. 1388-1394.
Sendamarai, et al., "Structure of the membrane proximal oxidoreductase domain of human Steap3, the dominant ferrireductase of the erythroid transferrin cycle," PNAS, vol. 105, No. 21, 2008, pp. 7410-7415.
Silliman, et al., "Identification of lipids that accumulate during the routine storage of prestorage leukoreduced red blood cells and cause acute lung injury," Transfusion, vol. 51, 2011, pp. 2549-2554.
Search Report and Written Opinion dated Sep. 4, 2015 for PCT/US2015/029552.
Tissot, et al., "Analysis and clinical relevance of microparticles from red blood cells," Curr. Opin. Hematol., vol. 17, No. 6, 2010, pp. 571-577.
Wright, et al., "Proteinchip(R) surface enhanced laser desorption/ionization (SELDI) mass spectrometry: a novel protein biochip technology for detection of prostate cancer biomarkers in complex protein mixtures," Prostate Cancer and Prostatic Dis., vol. 2, No. 5-6, 1999, pp. 264-276.
PCT International Search Report and Written Opinion, International Application No. PCT/US2015/029552 dated Sep. 4, 2015, 19 pp.
GenBank BC095421.1, *Homo Sapiens* STEAP Family Member 3, mRNA (cDNA Clone MGC:110951 Image:30336214), Complete Cds, Mar. 19, 2007 [online]. [Retrieved on Aug. 18, 2015.] Retrieved from the Internet <URL: http://www.ncbi.nlm.nih.gov/nuccore/BC095421> Entire document.
Sendamarai et al., "Structure of the Membrane Proximal Oxidoreductase Domain of Human Steap3, the Dominant Ferrireductase of the Erythroid Transferrin Cycle." Proc Natl Acad Sci USA, May 27, 2008, vol. 105, No. 21, pp. 7410-7415.
Lambe, et al., "Identification of a Steap3 Endosomal Targeting Motif Essential for Normal Iron Metabolism." Blood, Feb. 19, 2009, vol. 113, No. 8, pp. 1805-1808.

* cited by examiner

SEQUENCE LISTING

<160> NUMBER OF SEQ ID NOS: 4

<210> SEQ ID NO 1
<211> LENGTH: 488
<212> TYPE: PRT
<213> ORGANISM: Homo sapiens

<400> SEQUENCE: 1

```
Met Pro Glu Glu Met Asp Lys Pro Leu Ile Ser Leu His Leu Val Asp
1               5                   10                  15

Ser Asp Ser Ser Leu Ala Lys Val Pro Asp Glu Ala Pro Lys Val Gly
            20                  25                  30

Ile Leu Gly Ser Gly Asp Phe Ala Arg Ser Leu Ala Thr Arg Leu Val
        35                  40                  45

Gly Ser Gly Phe Lys Val Val Val Gly Ser Arg Asn Pro Lys Arg Thr
    50                  55                  60

Ala Arg Leu Phe Pro Ser Ala Ala Gln Val Thr Phe Gln Glu Glu Ala
65                  70                  75                  80

Val Ser Ser Pro Glu Val Ile Phe Val Ala Val Phe Arg Glu His Tyr
                85                  90                  95

Ser Ser Leu Cys Ser Leu Ser Asp Gln Leu Ala Gly Lys Ile Leu Val
            100                 105                 110

Asp Val Ser Asn Pro Thr Glu Gln Glu His Leu Gln His Arg Glu Ser
        115                 120                 125

Asn Ala Glu Tyr Leu Ala Ser Leu Phe Pro Thr Cys Thr Val Val Lys
    130                 135                 140

Ala Phe Asn Val Ile Ser Ala Trp Thr Leu Gln Ala Gly Pro Arg Asp
145                 150                 155                 160

Gly Asn Arg Gln Val Pro Ile Cys Gly Asp Gln Pro Glu Ala Lys Arg
                165                 170                 175

Ala Val Ser Glu Met Ala Leu Ala Met Gly Phe Met Pro Val Asp Met
            180                 185                 190

Gly Ser Leu Ala Ser Ala Trp Glu Val Glu Ala Met Pro Leu Arg Leu
        195                 200                 205

Leu Pro Ala Trp Lys Val Pro Thr Leu Leu Ala Leu Gly Leu Phe Val
    210                 215                 220

Cys Phe Tyr Ala Tyr Asn Phe Val Arg Asp Val Leu Gln Pro Tyr Val
225                 230                 235                 240

Gln Glu Ser Gln Asn Lys Phe Phe Lys Leu Pro Val Ser Val Val Asn
                245                 250                 255

Thr Thr Leu Pro Cys Val Ala Tyr Val Leu Leu Ser Leu Val Tyr Leu
            260                 265                 270

Pro Gly Val Leu Ala Ala Ala Leu Gln Leu Arg Arg Gly Thr Lys Tyr
        275                 280                 285

Gln Arg Phe Pro Asp Trp Leu Asp His Trp Leu Gln His Arg Lys Gln
    290                 295                 300

Ile Gly Leu Leu Ser Phe Phe Cys Ala Ala Leu His Ala Leu Tyr Ser
305                 310                 315                 320

Phe Cys Leu Pro Leu Arg Arg Ala His Arg Tyr Asp Leu Val Asn Leu
                325                 330                 335

Ala Val Lys Gln Val Leu Ala Asn Lys Ser His Leu Trp Val Glu Glu
            340                 345                 350

Glu Val Trp Arg Met Glu Ile Tyr Leu Ser Leu Gly Val Leu Ala Leu
        355                 360                 365
```

Gly Thr Leu Ser Leu Leu Ala Val Thr Ser Leu Pro Ser Ile Ala Asn
            370                 375                 380

Ser Leu Asn Trp Arg Glu Phe Ser Phe Val Gln Ser Ser Leu Gly Phe
385                 390                 395                 400

Val Ala Leu Val Leu Ser Thr Leu His Thr Leu Thr Tyr Gly Trp Thr
                405                 410                 415

Arg Ala Phe Glu Glu Ser Arg Tyr Lys Phe Tyr Leu Pro Pro Thr Phe
                420                 425                 430

Thr Leu Thr Leu Leu Val Pro Cys Val Val Ile Leu Ala Lys Ala Leu
                435                 440                 445

Phe Leu Leu Pro Cys Ile Ser Arg Arg Leu Ala Arg Ile Arg Arg Gly
            450                 455                 460

Trp Glu Arg Glu Ser Thr Ile Lys Phe Thr Leu Pro Thr Asp His Ala
465                 470                 475                 480

Leu Ala Glu Lys Thr Ser His Val
                485

<210> SEQ ID NO 2
<211> LENGTH: 3869
<212> TYPE: DNA
<213> ORGANISM: Homo sapiens

<400> SEQUENCE: 2

```
gaggaggagc ctcgggccga gccaccgcct tcgccgcgga ccttcagctg ccgcggtcgc      60
tccgagcggc gggccgcaga gccaccaaaa tgccagaaga gatggacaag ccactgatca     120
gcctccacct ggtggacagc gatagtagcc ttgccaaggt ccccgatgag gcccccaaag     180
tgggcatcct gggtagcggg gactttgccc gctccctggc cacacgcctg gtgggctctg     240
gcttcaaagt ggtggtgggg agccgcaacc ccaaacgcac agccaggctg tttccctcag     300
cggcccaagt gactttccaa gaggaggcag tgagctcccc ggaggtcatc tttgtggctg     360
tgttccggga gcactactct tcactgtgca gtcagtga ccagctggcg ggcaagatcc       420
tggtggatgt gagcaacccc acagagcaag agcaccttca gcatcgtgag tccaatgctg     480
agtacctggc ctcccctctc cccacttgca cagtggtcaa ggccttcaat gtcatctctg     540
cctggaccct gcaggctggc ccaagggatg gtaacaggca ggtgcccatc tgcggtgacc     600
agccagaagc caagcgtgct gtctcggaga tggcgctcgc catgggcttc atgcccgtgg     660
acatgggatc cctggcgtca gcctgggagg tgaggccat gcccctgcgc ctcctcccgg      720
cctggaaggt gcccaccctg ctggccctgg ggctcttcgt ctgcttctat gcctacaact     780
tcgtccggga cgttctgcag ccctatgtgc aggaaagcca gaacaagttc ttcaagctgc     840
ccgtgtccgt ggtcaacacc acactgccgt gcgtggccta cgtgctgctg tcactcgtgt     900
acttgcccgg cgtgctggcg gctgccctgc agctgcggcg cggcaccaag taccagcgct    960
tccccgactg gctggaccac tggctacagc accgcaagca gatcgggctg ctcagcttct    1020
tctgcgccgc cctgcacgcc ctctacagct tctgcttgcc gctgcgccgc gccaccgct    1080 acgacctggt caacctggca gtcaagcagg tcttggccaa caagagccac ctctgggtgg    1140
aggaggaggt ctggcggatg gagatctacc tctccctggg agtgctggcc tcggcacgt    1200 tgtccctgct ggccgtgacc tcactgccgt ccattgcaaa ctcgctcaac tggagggagt    1260
tcagcttcgt tcagtcctca ctgggctttg tggccctcgt gctgagcaca ctgcacacgc    1320
tcacctacgg ctggacccgc gccttcgagg agagccgcta caagttctac ctgcctcca    1380 ccttcacgct cacgctgctg gtgccctgcg tcgtcatcct ggccaaagcc ctgtttctcc    1440
```

```
tgccctgcat cagccgcaga ctcgccagga tccggagagg ctgggagagg gagagcacca    1500
tcaagttcac gctgcccaca gaccacgccc tggccgagaa gacgagccac gtatgaggtg    1560
cctgccctgg gctctggacc ccgggcacac gagggacggt gccctgagcc cgttaggttt    1620
tcttttcttg gtggtgcaaa gtggtataac tgtgtgcaaa taggaggttt gaggtccaaa    1680
ttcctgggac tcaaatgtat gcagtactat tcagaatgat atacacacat atgtgtatat    1740
gtatttacat atattccaca tatataacag gatttgcaat tatacatagc tagctaaaaa    1800
gttgggtctc tgagatttca acttgtagat ttaaaaacaa gtgccgtacg ttaagagaag    1860
gcagatcatg ctattgtgac atttgcagag atatacacac actttttgta cagaagaggc    1920
ttgtgctgtg gtgggttcga tttatccctg cccaccccac ccccacaact tcccttttgc    1980
tacttcccca aggctcttgc agagctaggg ctctgaaggg gagggaaggc aacggctctg    2040
cccagagcca tccctggagc atgtgagcag cggctggtct cttccctcca cctggggcag    2100
cagcaggagg cctggggagg aggaaaatca ggcagtcggc ctggagtctg tgcctggtcc    2160
tttgcccggt ggtgggagga tggagggatt gggctgaagc tgctccacct catccttgct    2220
gagtggggga gacattttcc ctgaaagtca gaagtcacca tagagcctgc aaatggatcc    2280
tcctgtgaga gtgacgtcac ctcctttcca gagccattag tgagcctggc ttgggaacaa    2340
gtgtaatttc cttccctcct ttaacctggc gatgagcgtc cttaaaacca ctgtgccttc    2400 tcacccttc catcttcagt ttgaatgact cccaggaagg cctagagcag acccttaga     2460 aatcagccca agggggagag caagagaaaa cactctaggg agtaaagctc cccgggcgtc    2520
agagttgagc cctgcctggg ctgaaggact gtcttcacga agtcagtcct gaggaaaaat    2580 attgggact ccaaatgtcc tctggcagag gacccagaaa accacactgg ctccaacttc     2640
ctcctcatgg ggcattacac ttcaaaacag tggggagcaa cttttccacc aaagctacaa    2700
acctaaaatg ctgctgcccc aaagcacaag agggaagagc accgccgggg ccacaggacg    2760
tctgtcctcc agtcacaggc catccttgct gctccctact gactctagct tacttcccct    2820
gtgaagaaac aggtgttctc ggctgagccc ccaaccctct gcagaaccag gttgatctgc    2880
cacagaaaaa gcatctttga agacaaagag ggtgaggtct tcatgagtct cctgggccca    2940
aagccatctt ctgatggaag gaagagagta gggccagtga aggctgccca gagagaatgt    3000
cacagatgag gctgccctg ccccccccc gccaggagg tttcatgagc tcatgtctat        3060
gcagcacata agggttcttc agtgaaaagc aggagaagag cccactgcaa ggatagctca    3120
ttaggcacat gaccgatgca gggaaggcca tgccggggaa gctcttcctg caggtattt     3180 ccatctgctg tgccaaggct gagcggcaga aacttgtctc ataaattggc actgatggag    3240
catcagctgt ggcccacaga gagccttgct gagaagggg caggtaaagc agagatttta    3300
gcattgcctt ggcataacaa gggcccatcg attccctact aatgagaggc agggagagca    3360
tgggcaatgg agacccacca atgatcccca accccgtgg gtactggctg cctgccctgg    3420
gccagggaat ggctccttat accaaagatg ctggcacata gcagaaccca gtgcacgtcc    3480
tccccttccc acccacctct ggctgaaggt gctcaagagg gaagcaatta taaggtgggt    3540
ggcaggaggg aacaggtgcc acctgctgga caatcacacg aaaggcaggc gggctgtgta    3600
ctggggcctg actgtgcgtc cactgctgtc ttccctacct caccaggcta ctggcagcag    3660
catcccgaga gcacatcatc tccacagcct ggtaaattcc atgtgcctct gggtacaaaa    3720
gtgcctcaac gacatgctct ggaaatccca aatgccacag tctgaggttg atatctaaaa    3780
```

-continued

```
tctatgcctt caaaagagtc tctgttttt tttttaacc tggtagacag tataaaagca      3840
gtgcaaataa acacctaacc ttctgcaaa                                      3869
```

<210> SEQ ID NO 3
<211> LENGTH: 488
<212> TYPE: PRT
<213> ORGANISM: Mus musculus

<400> SEQUENCE: 3

```
Met Ser Gly Glu Met Asp Lys Pro Leu Ile Ser Arg Arg Leu Val Asp
1               5                   10                  15

Ser Asp Gly Ser Leu Ala Glu Val Pro Lys Glu Ala Pro Lys Val Gly
            20                  25                  30

Ile Leu Gly Ser Gly Asp Phe Ala Arg Ser Leu Ala Thr Arg Leu Val
        35                  40                  45

Gly Ser Gly Phe Ser Val Val Val Gly Ser Arg Asn Pro Lys Arg Thr
    50                  55                  60

Ala Gly Leu Phe Pro Ser Leu Ala Gln Val Thr Phe Gln Glu Glu Ala
65                  70                  75                  80

Val Ser Ser Pro Glu Val Ile Phe Val Ala Val Phe Arg Glu His Tyr
                85                  90                  95

Ser Ser Leu Cys Ser Leu Ala Asp Gln Leu Ala Gly Lys Ile Leu Val
            100                 105                 110

Asp Val Ser Asn Pro Thr Glu Lys Glu His Leu Gln His Arg Gln Ser
        115                 120                 125

Asn Ala Glu Tyr Leu Ala Ser Leu Phe Pro Ala Cys Thr Val Val Lys
    130                 135                 140

Ala Phe Asn Val Ile Ser Ala Trp Ala Leu Gln Ala Gly Pro Arg Asp
145                 150                 155                 160

Gly Asn Arg Gln Val Leu Ile Cys Ser Asp Gln Pro Glu Ala Lys Arg
                165                 170                 175

Thr Ile Ser Glu Met Ala Arg Ala Met Gly Phe Thr Pro Leu Asp Met
            180                 185                 190

Gly Ser Leu Ala Ser Ala Arg Glu Val Glu Ala Ile Pro Leu Arg Leu
        195                 200                 205

Leu Pro Ser Trp Lys Val Pro Thr Leu Leu Ala Leu Gly Leu Phe Val
    210                 215                 220

Cys Phe Tyr Thr Tyr Asn Phe Ile Arg Asp Val Leu Gln Pro Tyr Ile
225                 230                 235                 240

Arg Lys Asp Glu Asn Lys Phe Tyr Lys Met Pro Leu Ser Val Val Asn
                245                 250                 255

Thr Thr Leu Pro Cys Val Ala Tyr Val Leu Leu Ser Leu Val Tyr Leu
            260                 265                 270

Pro Gly Val Leu Ala Ala Leu Gln Leu Arg Arg Gly Thr Lys Tyr
        275                 280                 285

Gln Arg Phe Pro Asp Trp Leu Asp His Trp Leu Gln His Arg Lys Gln
    290                 295                 300

Ile Gly Leu Leu Ser Phe Phe Ala Met Leu His Ala Leu Tyr Ser
305                 310                 315                 320

Phe Cys Leu Pro Leu Arg Arg Ser His Arg Tyr Asp Leu Val Asn Leu
                325                 330                 335

Ala Val Lys Gln Val Leu Ala Asn Lys Ser Arg Leu Trp Ala Glu Glu
            340                 345                 350
```

```
Glu Val Trp Arg Met Glu Ile Tyr Leu Ser Leu Gly Val Leu Ala Leu
            355                 360                 365

Gly Met Leu Ser Leu Leu Ala Val Thr Ser Leu Pro Ser Ile Ala Asn
    370                 375                 380

Ser Leu Asn Trp Lys Glu Phe Ser Phe Val Gln Ser Thr Leu Gly Phe
385                 390                 395                 400

Val Ala Leu Ile Leu Ser Thr Met His Thr Leu Thr Tyr Gly Trp Thr
                405                 410                 415

Arg Ala Phe Glu Glu Asn His Tyr Lys Phe Tyr Leu Pro Pro Thr Phe
                420                 425                 430

Thr Leu Thr Leu Leu Pro Cys Val Ile Ile Leu Ala Lys Gly Leu
            435                 440                 445

Phe Leu Leu Pro Cys Leu Asn Arg Arg Leu Thr Lys Ile Arg Arg Gly
450                 455                 460

Trp Glu Lys Asp Gly Ala Val Lys Phe Met Leu Pro Gly Asp His Thr
465                 470                 475                 480

Gln Gly Glu Lys Thr Ser His Val
                485

<210> SEQ ID NO 4
<211> LENGTH: 3142
<212> TYPE: DNA
<213> ORGANISM: Mus musculus

<400> SEQUENCE: 4
tcacactcta tctcagacct tgagctaaag gactctccca aggcgagggg gccactgctt      60 actgggccc tccacctggg aaggagaggt taaaggtgac ccagggttaa ggagaacctg     120
gtatgccaca tctcaactta tgatgtgagc tccagccacc cagcttcaga agaaatggct     180
gcagaggccc acaggcagca gggctcttgc cccaccatcc cctcagaggg ctgtggaaag     240
tcaccagaga agaaaggcag tgcggccgac tctagacctg gtgagctgga gtctgtgggg     300
cagggaggaa gcagggcata aagacacag gaagcaactc tgccctgatt ccagactcca     360
tctgcatgga ctgattccag gtgctagggt tcctttctca gaaacccag aagtccacga     420 aggcactgct atgtcggggg agatggacaa gccgctgatc agccgccgcc tagtggacag     480
tgatggcagt ctggctgagg tccccaagga ggccccaaa gtgggcatcc tgggcagtgg     540 ggatttgcc cgttccctgg ccacacgcct ggtgggctct ggcttcagtg tggtggtggg     600
gagccgtaac cccaaacgca cggctggcct cttccctcc ttagctcaag tgactttcca     660
ggaggaagcc gtgagctctc cagaggtcat ctttgtggcc gtgttccggg agcactattc     720
ctcactgtgc agtctcgctg accagttggc tggcaagatc ctcgtggatg taagcaaccc     780
cacggagaag gagcatcttc agcaccgcca gtctaacgct gagtacctgg cctcactctt     840
tcctgcgtgc actgtggtga aggccttcaa cgtcatctct gcatgggccc tacaggctgg     900
cccaagggat gggaacaggc aggtgctcat ctgcagtgat cagccagaag ccaagcgcac     960
catctcagag atggcacgcg ccatgggttt cacacccctg acatgggat ccctggcctc    1020 agcgagggag gtagaagcca tacccctgcg cctccttcca tcctggaagg tgcccaccct    1080
cctggcactg gggctctttg tgtgcttcta cacctacaac ttcatccgag acgttctaca    1140
gccatacatt cggaaagatg agaacaagtt ctacaagatg cccttgtctg tggtcaacac    1200
cacactaccc tgtgtggctt atgtgctgct gtccctagtg tacctgcccg gtgtgctggc    1260
agctgcgctt cagctgcgga gggggaccaa gtaccagcgc ttcccagact ggctggacca    1320
```

```
ctggctgcag catcgcaagc agatcgggct gctcagcttc ttcttcgcga tgctgcacgc    1380
tctctacagc ttctgcctgc cgctgcgccg ctcccaccgc tacgacctgg tcaatctggc    1440
tgtgaagcag gtcctggcca acaagagccg cctctgggct gaggaagaag tctggaggat    1500
ggagatatac ctgtccctgg gtgtgctggc cctgggcatg ttgtcgctgc tggctgtcac    1560
ctcgctcccg tccattgcta attccctcaa ctggaaggag ttcagcttcg tgcagtccac    1620
actgggcttc gtggccctga tactcagcac aatgcacaca ctcacctacg gctgacccg     1680 tgcctttgag gaaaaccact acaagttcta cctgccgccc acattcacac tcacgctgct    1740
cctgccctgt gtgatcatcc tggccaaggg cctcttcctc ctgccctgcc tcaaccgcag    1800
actcaccaag atacgcaggg gctgggagaa agatggggct gtcaagttca tgctgcccgg    1860
cgaccacaca caggggggaga aaacaagcca cgtgtgaggc cctggaagtg gagatggctt    1920 gtggggccc  tgagctgggt tcgggtctct tttctggatg ctgcacagcg aggtgatgat    1980
atatgcgtgg gtggctgaga tcctaattcc tgggatgcag gtgtaaactg acatactcag    2040
aatgacaccc catacatgtg atatgtactt acatatattt cacatataat aagatttgct    2100
attattctta cttagctaaa aaaaaaaagt gggtccctat atttcagcgt aagcatttca    2160
aagcaaatgc cacacattga acagcagatc ccaccccttgt ggtatctaca gaggcagaca    2220
gacactctgg tataggagaa actgtctttc gttggattct ctcctttaat ctctatgctc    2280
cttattagct gaatcctaaa gttggtgcaa agctggggca agaaatgcct ctggtgccgc    2340 ctaccccat  cccagggcta agaaagaagc ctcgagtgaa cagggaacca ggtctggact    2400
ctgctgcttc cctgggcgtg cgtggggagg ctcagcaaga cccctggga tctatgcagg     2460 agcttttca  ggtccgtcct ttcttcaggg aagggtctga agctgcccca tctgatccta    2520
gctgagctga aagattctt cccccacccc tgaaagtcca gagtcaccac cggagcctgc     2580
aaattgatcc ttctgcgaag gtgtgaagtc accgcctctc cagagccatt aatgaacctg    2640
gtcttcggga ggaggataat tgtttcctct ccattaagtt gctggtgacc cccccttaa     2700 atcactgtgc cttctcgcct tttccatcat taatttggac atctccgtgg agtggacact    2760
tgtctgggca gtccggggtg ggggggagca ttagagattg cagagaataa ccatcgaatc    2820
ctcttcttgg ggcaaccctc cccttggatg tgccccaggc ctgccttcat taaattggtc    2880
cctgaggaga ataataggga ccctttttcat ttaccctgtc gcctgtaggc agaaaaccta    2940
ccttctgagc acccagaaaa cacagtggcc ccatgctctt cttcagggg  ttccacagcc    3000 cccttccccg tgttttttgcc tccctccctc cttcctcccc tccctccctc cctcactgtt    3060
acgttcaacc acaaaagtct tcaaatattg ttttttttgaa ttcttaaaga gacctcattt    3120
tattacaaaa aaaaaaaaaa aa                                             3142
```

STEAP3 AS A BIOCHEMICAL MARKER OF RED BLOOD CELL STORAGE AND TOXICITY

CROSS-REFERENCE TO RELATED APPLICATIONS

This application is the National Stage of International Application No. PCT/US2015/029552, filed May 6, 2015, and claims the benefit of U.S. Provisional Application No. 61/989,440 filed May 6, 2014, the entire disclosure of which are hereby incorporated by reference in their entirety for all purposes.

SEQUENCE LISTING

This application contains a Sequence Listing which has been filed electronically in ASCII format and is hereby incorporated by reference in its entirety. Said ASCII copy, created on Jun. 11, 2017, is named 29382US_CRF_SequenceListing.txt and is 18,116 bytes in size.

FIELD

The disclosure relates to compositions and methods for determining post-transfusion survival and toxicity of red blood cell (RBC) units by measuring the levels of one or more markers in a RBC sample.

BACKGROUND

In excess of 15,000,000 units of RBCs are transfused in the USA each year into an excess of 5,000,000 patients (approximately 1 out of every 65 Americans). Currently, there are only 3 quality control measures utilized prior to release of a unit of RBCs: 1) testing negative for the screened pathogens, 2) compatibility with the patient regarding recipient antibodies to donor antigens, and 3) storage history of 4° C. FDA guidelines for RBC storage require that stored RBCs (up to 42 days) have less than 1% hemolysis and have 75% 24 hour post-transfusion survival, on average for a given storage system. However, it has been appreciated for over forty years that there is tremendous variability in how individual units of RBCs store from different human donors[1,2]. Even for current blood storage solutions, 24 hour post-transfusion recoveries range from 35% to 100%[2] It has been further observed that RBC storage is reproducible from donation to donation for a given donor[3,4], suggesting a potential genetic component[1,5]. Despite extensive study, there is no measurable entity known to predict how an RBC unit will do when transfused. For this reason, currently, there are no quality control measures (or unit release criteria) regarding quality of RBC units.

This is a medical problem for a number of reasons. First, RBCs that survive poorly post-transfusion result in a less efficacious product from the standpoint of RBC replacement. However, even more important is the notion that RBCs that are cleared from circulation represent a toxic insult to the recipient, which may result in morbidity and/or mortality. A second issue is what biochemical markers may predict RBCs that are going to be toxic from pathways other than simple RBC clearance.

There are currently no existing techniques to predict post-transfusion survival of RBC units or toxicity of said units. Thus, the present disclosure satisfies these and other needs. Disclosed herein is a method for assessing a RBC unit (prior to transfusion) allowing the prediction of its post-transfusion survival and toxicity. Specifically, biochemical markers that predict if RBCs will survive well post-transfusion or will be toxic are presented herein.

SUMMARY

Described herein are compositions and methods for determining post-transfusion survival and toxicity of a RBC unit by measuring the levels of one or more markers, including Steap3, in a RBC sample.

In a first aspect, disclosed herein is a method of determining post-transfusion survival of red blood cells (RBC) prior to transfusion, the method comprising the steps of: a) providing a sample of RBC; b) measuring the level of activity of Steap3 protein in the RBC sample; c) comparing the level of activity of Steap3 protein in the RBC sample with the level of Steap3 protein activity in a control RBC sample, wherein a higher level of activity of Steap3 protein in the RBC sample as compared to the control sample is indicative of a lower RBC storage quality.

In a second aspect, disclosed herein is a method of determining the suitability of a red blood cell (RBC) unit for transfusion, the method comprising the steps of: a) providing a sample of RBC; b) measuring the level of activity of Steap3 protein in the RBC sample; c) comparing the level of activity of Steap3 protein in the RBC sample with the level of Steap3 protein activity in a control sample, wherein a higher level of activity of Steap3 protein in the RBC sample is indicative of a lower suitability for transfusion.

In various embodiments of the first and second aspects, the measurement is performed at the time of collection of the RBC sample.

In various embodiments of the first and second aspects, the measurement is performed during the time of storage of the RBC sample.

In various embodiments of the first and second aspects, the measurement of activity is performed by determining ferric reductase activity.

In various embodiments of the first and second aspects, the is 2-200 fold higher than in the control sample.

In a third aspect, disclosed herein is a method of evaluating the suitability of a human subject to be blood donor comprising: (a) providing a biological sample from the human subject, wherein the sample comprises all, or a portion of, an Steap3 gene; and (b) detecting the presence of a polymorphism in the Steap3 gene or the portion thereof in the sample, wherein the Steap3 gene comprises at least 90% sequence identity to SEQ ID NO: 2; and (c) evaluating the human subject for suitability as a blood donor based on the presence of a polymorphism in the Steap3 gene or the portion thereof.

In various embodiments of the third aspect, the polymorphism in the Steap3 gene results in a A>V substitution at position 350 of the protein sequence.

In various embodiments of the third aspect, the polymorphism in the Steap3 gene results in reduced activity of the Steap3 protein.

In a fourth aspect, disclosed herein is a method of evaluating the suitability of a human subject to be blood donor comprising: (a) providing a biological sample from the human subject; and (b) determining the level of Steap3 protein activity in the sample; and (c) evaluating the human subject as being an unsuitable blood donor based on the a higher level of Steap3 protein activity in the sample as compared to the activity in a control sample.

In various embodiments of the fourth aspect, the protein activity is ferric reductase activity.

In a fifth aspect, disclosed herein is a method for determining RBC storage quality, the method comprising the steps of: obtaining a dataset associated with a sample of stored blood, wherein the dataset comprises a Steap3 marker; analyzing the dataset to determine data for the Steap3 marker, wherein the data is positively correlated or negatively correlated with RBC storage quality of the sample of stored blood.

In various embodiments of the fifth aspect, the data is protein level, mRNA level protein activity level, or sequence of the Steap3 protein or nucleic acid.

In a sixth aspect, disclosed herein is a method for determining RBC storage quality, the method comprising the steps of: providing a sample of stored blood, wherein the sample comprises a Steap3 marker; contacting the sample with a reagent; generating a complex between the reagent and the Steap3 marker; detecting the complex to obtain a dataset associated with the sample, wherein the dataset comprises expression or activity level or sequence data for the Steap3 marker; and analyzing the expression or activity level data for the a Steap3 marker, wherein the expression or activity level or sequence of the a Steap3 marker is positively correlated or negatively correlated with RBC storage quality.

In a seventh aspect, disclosed herein is a computer-implemented method for determining RBC storage quality, the method comprising the steps of: storing, in a storage memory, a dataset associated with a stored blood sample, wherein the dataset comprises data for a Steap3 marker; and analyzing, by a computer processor, the dataset to determine the expression or activity levels or sequence of the Steap3 marker, wherein the expression or activity levels or sequence are positively correlated or negatively correlated with RBC storage quality.

In an eighth aspect, disclosed herein is a system for determining RBC storage quality, the system comprising: a storage memory for storing a dataset associated with a stored blood sample, wherein the dataset comprises data for a Steap3 marker; and a processor communicatively coupled to the storage memory for analyzing the dataset to determine the activity or expression levels or sequence of the Steap3 marker, wherein the activity or expression levels or sequence are positively correlated or negatively correlated with RBC storage quality.

In a ninth aspect, disclosed herein is a computer-readable storage medium storing computer-executable program code, the program code comprising: program code for storing a dataset associated with a stored blood sample, wherein the dataset comprises data for a Steap3 marker; and program code for analyzing the dataset to determine the activity or expression levels or sequence of the Steap3 marker, wherein the activity or expression levels or sequence of the markers arc positively correlated or negatively correlated with RBC storage quality.

In a tenth aspect, disclosed herein is a method for predicting a negative transfusion outcome, the method comprising the steps of: obtaining a dataset associated with a sample of stored blood, wherein the dataset comprises data for a Steap3 marker; analyzing the dataset to determine data for the at least one marker, wherein the data is positively correlated or negatively correlated with a negative transfusion outcome if the blood sample is transfused into a patient.

In an embodiment of the tenth aspect, the data is protein level, mRNA level, protein activity level, or sequence of the Steap3 protein or nucleic acid.

In an eleventh aspect, disclosed herein is a method for predicting a negative transfusion outcome, the method comprising the steps of: providing a sample of stored blood, wherein the sample comprises a Steap3 marker; contacting the sample with a reagent; generating a complex between the reagent and the Steap3 marker; detecting the complex to obtain a dataset associated with the sample, wherein the dataset comprises expression or activity level or sequence data for the Steap3 marker; and analyzing the expression or activity level data for the markers, wherein the expression or activity level or sequence of the at least one marker is positively correlated or negatively correlated with a negative transfusion outcome if the blood sample is transfused into a patient.

In a twelfth aspect, disclosed herein is a computer-implemented method for predicting a negative transfusion outcome, the method comprising the steps of: storing, in a storage memory, a dataset associated with a stored blood sample, wherein the dataset comprises data for a Steap3 marker; and analyzing, by a computer processor, the dataset to determine the expression or activity levels or sequence of the Steap3 marker, wherein the expression or activity levels or sequence are positively correlated or negatively correlated with a negative transfusion outcome if the blood sample is transfused into a patient.

In a thirteenth aspect, disclosed herein is a system for predicting a negative transfusion outcome, the system comprising: a storage memory for storing a dataset associated with a stored blood sample, wherein the dataset comprises data for a Steap3 marker: and a processor communicatively coupled to the storage memory for analyzing the dataset to determine the activity or expression levels or sequence of the Steap3 marker, wherein the activity or expression levels or sequence are positively correlated or negatively correlated with a negative transfusion outcome if the blood sample is transfused into a patient.

In a fourteenth aspect, disclosed herein is a computer-readable storage medium storing computer-executable program code, the program code comprising: program code for storing a dataset associated with a stored blood sample, wherein the dataset comprises data for a Steap3 marker; and program code for analyzing the dataset to determine the activity or expression levels of the Steap3 marker, wherein the activity or expression levels or sequence of the markers are positively correlated or negatively correlated with a negative transfusion outcome if the blood sample is transfused into a patient.

In embodiments of the method or storage medium or system of the aspects above, the dataset is obtained at the time of collection of the RBC sample.

The method or storage medium or system of any one of the aspects above, wherein the dataset is obtained during the time of storage of the RBC sample.

In embodiments of the method or storage medium or system of the aspects above, the dataset is obtained by determining ferric reductase activity.

In a fifteenth aspect, disclosed herein is a method for determining post-transfusion survival of red blood cells (RBC) prior to transfusion comprising: a) generating data on the level of Steap3 in a sample front the subject; b) generating data on the level of at least one additional biomarker or indicator of blood storage c) generating a score by mathematically combining the data in (a) and (b), wherein the score is indicative of post-transfusion survival of red blood cells (RBC) in the sample.

In an embodiment of the fifteenth aspect, the score is used to determine whether the RBC sample will be administered to the subject.

In an embodiment of the fifteenth aspect, the score is generated by a computer processor.

In various embodiments of the above, the method further comprises the step of administering or not administering the RBC sample that has been tested.

In a sixteenth aspect, disclosed herein is a kit for use in predicting a negative transfusion outcome or red blood cell (RBC) storage quality, the kit comprising: a set of reagents comprising a plurality of reagents for determining from a stored blood sample data for Steap3 marker; and instructions for using the plurality of reagents to determine data from the stored blood sample.

In various embodiments of the sixteenth aspect, data is protein level, mRNA level, protein activity level, or sequence of the Steap3 protein or nucleic acid.

DETAILED DESCRIPTION

Figure 1A:
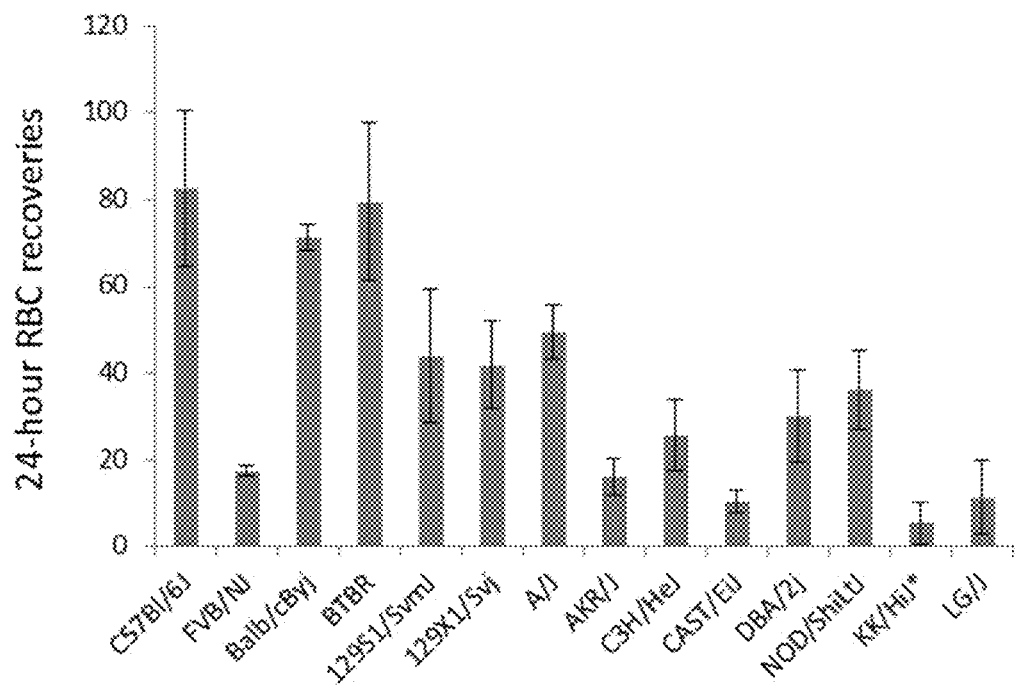
FIGS. 1A-1C show the correlation between Steap3 activity and RBC storage.

The present invention generally relates to compositions and methods for determining post-transfusion survival and toxicity of RBCs by measuring the levels of one or more markers in a RBC sample.

The invention described in this disclosure represents a method for assessing an RBC unit (prior to transfusion) allowing the prediction of its post-transfusion survival and toxicity. Among the specific aims are: (1) Biochemical markers that predict if RBCs will survive well post-transfusion; and (2) Biochemical markers that predict if RBCs are toxic post-transfusion.

Red blood cell (RBC) transfusion is a life-saving therapy, and refrigerated storage is crucial for maintaining an adequate supply of donor units. However, recent studies have focused on potential adverse clinical sequelae resulting front transfusing humans with RBC units stored for longer periods of time. Indeed, multiple observational studies in human patients provide data demonstrating inferior clinical outcomes when older, stored RBC units are transfused[1]. Nonetheless, this issue remains controversial because other, similarly designed human studies, show no difference in clinical outcome when comparing patients receiving transfusions of older or fresher RBC units[1,2]. To begin to address this controversy, several prospective human trials are currently ongoing, and one was recently completed[3-5]. However, it is not controversial that stored RBCs accumulate multiple factors that may be toxic when infused (e.g. microparticles, free iron, free hemoglobin, prostaglandins, and leukotrienes)[6-14].

One complication in studying RBC transfusion is that there is considerable donor-to-donor variation in the effect of refrigerated storage on RBC function and quality. In addition, there is a general absence of robust analytic tests that consistently and accurately predict the quality of a given RBC unit prior to transfusion[15]. Due to the genetic and environmental complexity of outbred human donor populations, and the difficulty in limiting the number of independent variables in studying human RBC transfusion, we developed a robust animal model to begin to address these issues[16]. Using inbred mouse strains in defined environmental and dietary settings limits the experimental variability of the system, and allows for deliberate manipulation of independent variables.

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

As used herein, "RBC storage quality" is defined as the extent of post-transfusion recovery of the stored RBCs; higher recovery is defined as higher quality. Examples of post-transfusion recovery include greater than zero and almost 100% recovery, i.e., recovery of 10%, 20%, 30%, 40%, 50%, 60%, 70%, 80%, 90%, 100%, and all percentages in between. In one embodiment, an acceptable RBC storage quality is an average of 75% post-transfusion recovery at 24 hours, as under FDA guidelines.

As used herein, "toxicity" of a RBC unit is defined as any adverse reaction associated with transfusion of a RBC unit, including, but not limited to, hemolytic transfusion reactions, exposure to free hemoglobin, iron overload, induction of recipient cytokines, introduction of procoagulant activity, and inhibition of recipient vascular relaxation, among others.

As used herein, a RBC unit is less suitable for transfusion if it has lower RBC quality (i.e., lower post-transfusion survival) or elevated toxicity as compared to other RBC units, e.g., as compared to a control.

An "analyte" or "target" refers to a compound to be detected. Such compounds can include small molecules, peptides, proteins, nucleic acids, as well as other chemical entities. In the context of the present invention, an analyte or target will generally correspond to the biochemical compounds disclosed herein, or a reaction product thereof.

To "analyze" includes determining a value or set of values associated with a sample by measurement of analyte levels in the sample. "Analyze" may further comprise comparing the levels against constituent levels in a sample or set of samples from the same subject or other subject(s). For example, the blood storage markers, such as Steap3, of the present teachings can be analyzed by any of various conventional methods known in the art.

The term "biomarker" refers to a molecule (typically small molecule, protein, nucleic acid, carbohydrate, or lipid) that is expressed and/or released from a cell, which is useful for identification or prediction. Such biomarkers are molecules that can be differentially expressed, e.g., overexpressed or underexpressed, or differentially released in response to varying conditions (e.g., storage). In the context of the present invention, this frequently refers to Steap3 as disclosed herein, which shows altered levels of activity in stored versus non-stored RBCs, for instance, 1-fold, 2-fold, 3-fold, 4-fold, 5-fold or more in stored RBCs versus non-stored RBCs.

A "sample" refers to any source which is suspected of containing an analyte or target molecule. Examples of samples which may be tested using the present invention include, but are not limited to, blood, serum, plasma, urine, saliva, cerebrospinal fluid, lymph fluids, tissue and tissue and cell extracts, cell culture supernantants, among others. A sample can be suspended or dissolved in liquid materials such as buffers, extractants, solvents, and the like. In the context of the present application, a sample is generally a stored RBC sample of varying length of storage.

The term "subject" encompasses a cell, tissue, or organism, human or non-human, whether in vivo, ex vivo, or in vitro, male or female.

The term "generating data" encompasses obtaining a set of data determined from at least one sample. Generating data encompasses obtaining a sample, and processing the sample to experimentally determine the data. The phrase also encompasses receiving a set of data, e.g., from a third party that has processed the sample to experimentally determine the data. Additionally, the phrase encompasses mining data from at least one database or at least one publication or a combination of databases and publications. Data can be obtained by one of skill in the art via a variety of known ways including stored on a storage memory. Obtaining data encompasses data which has been generated from a sample, or data which has been obtained from sources such as patient medical history and records, physical examinations, treatment history, and the like.

The term "clinical factor" refers to a measure of a condition of a subject, e.g., disease activity or severity. "Clinical factor" encompasses all indicators of a subject's health status, including non-sample markers, and/or other characteristics of a subject, such as, without limitation, age and gender. A clinical factor can be a score, a value, or a set of values that can be obtained from evaluation of a sample (or population of samples) from a subject or a subject under a determined condition.

The term "algorithm" encompasses any formula, model, mathematical equation, algorithmic, analytical or programmed process, or statistical technique or classification analysis that takes one or more inputs or parameters, whether continuous or categorical, and calculates an output value, index, index value or score. Examples of algorithms include but are not limited to ratios, sums, regression operators such as exponents or coefficients, biomarker value transformations and normalizations (including, without limitation, normalization schemes that are based on clinical parameters such as age, gender, ethnicity, etc.), rules and guidelines, statistical classification models, and neural networks trained on populations. Also of use in the context of blood storage factors are linear and non-linear equations and statistical classification analyses to determine the relationship between (a) levels of blood storage markers, such as Steap3, detected in a subject sample and (b) the level of blood storage or blood quality from the respective subject.

"Antibody" refers to any immunoglobulin or intact molecule as well as to fragments thereof that bind to a specific epitope that may be used in the practice of the present invention. Such antibodies include, but are not limited to polyclonal, monoclonal, chimeric, humanized, single chain, Fab, Fab', F(ab)' fragments and/or F(v) portions of the whole antibody and variants thereof. All isotypes are encompassed by this term and may be used in the practice of this invention, including IgA, IgD, IgE, IgG, and IgM.

An "antibody fragment" refers specifically to an incomplete or isolated portion of the full sequence of the antibody which retains the antigen binding function of the parent antibody and may also be used in the present invention. Examples of antibody fragments include Fab, Fab', F(ab')2, and Fv fragments; diabodies; linear antibodies; single-chain antibody molecules; and multi specific antibodies formed from antibody fragments.

An intact "antibody" for use in the invention comprises at least two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. The term antibody includes antigen-binding portions of an intact antibody that retain capacity to bind. Examples of binding include (i) a Fab fragment, a monovalent fragment consisting of the $V_L$, $V_H$, $C_L$ and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et at., Nature, 341:544-516 (1989)), which consists of a VH domain; and (vi) an isolated complementarity determining region (CDR).

"Single chain antibodies" or "single chain Fv (scFv)" may also be used in the present invention. This term refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments can be prepared by recombinant techniques or enzymatic or chemical cleavage of intact antibodies.

A "monoclonal antibody" may be used in the present invention. Monoclonal antibodies are a preparation of antibody molecules of single molecular composition. A monoclonal antibody composition displays a single binding specificity and affinity for a particular epitope.

In one embodiment, the antibody or fragment is conjugated to an "effector" moiety. The effector moiety can be any number of molecules, including labeling moieties such as radioactive labels or fluorescent labels.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

Samples of RBCs stored for various amounts of time are compared to "control" samples which can be freshly drawn RBCs or RBCs which have been minimally stored. Control samples are assigned a relative analyte amount or activity to which sample values are compared. Relevant levels of analyte elevation occur when the sample amount or activity value relative to the control is 110%, more preferably 150%, more preferably 200-500% (i.e., two to five fold higher relative to the control), more preferably 1000-3000% higher. Alternatively, relevant levels of analyte decrease occur when the sample amount or activity value relative to the control is 90%, more preferably 50%, more preferably 20-50% (i.e., two to five fold lower relative to the control), inure preferably 20-100% lower.

Assays for many of the biochemical compounds disclosed herein are known or commercially available.

For example, antibody reagents can be used in assays to detect the levels of analytes in RBC samples using any of a number of immunoassays known to those skilled in the art.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., Curr. Opin. Biotechnol., 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (META); immunohistochemical (IHC) assays; capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See. e.g., Schmalzing et al., Electrophoresis, 18;2184-93 (1997); Bao, J. Chromatogr. B. Biomed. Sci., 699:463-80 (1997). Liposome immunoassays, such as flow-injection liposome immunoassays and liposome immunosensors, are also suitable for use in the present invention. See, e.g., Rongen et al., J. Immunol. Methods, 204: 105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., J. Clin. Chem. Clin. Biochem., 27:261-276 (1989)).

Specific immunological binding of the antibody to proteins can be detected directly or indirectly. Direct labels include fluorescent or luminescent tags, metals, dyes, radionuclides, and the like, attached to the antibody. A chemiluminescence assay using a chemiluminescent antibody specific for the protein is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is delectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}I$; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

In some embodiments, the measurement of the markers of the present invention is performed using various mass spectrometry methods. As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107, 623, entitled "Methods and Apparatus for Tandem Mass Spectrometry;" U.S. Pat. No. 6,268,144, entitled "DNA Diagnostics Based On Mass Spectrometry;" U.S. Pat. No.

6,124,137, entitled "Surface-Enhanced Photolabile Attachment And Release For Desorption And Detection Of Analytes;" Wright et al., Prostate Cancer and Prostatic Diseases 1999, 2:264-76; and Merchant and Weinberger, Electrophoresis 2000, 21; 1164-67.

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

Steap3

The Steap3 gene encodes a metalloreductase with the activity of coverting iron from an insoluble ferric ($Fe^{3+}$) to a soluble ferrous ($Fe^{2+}$) form.

Reference sequences for the mouse gene and protein have the NCBI accession numbers NM_001085409 and NP_001078878. The human gene and protein have the NCBI accession number NM_001008410. Representative sequences of Steap3 genes and proteins are shown below.

TABLE 1

| SEQ ID NO | Accession Number And Description | Amino acid/nucleotide sequence |
|---|---|---|
| 1 | NM_001008410 Human protein | MPEEMDKPLISLHLVDSDSSLAKVPDEAPKVGILGSGDFARS LATRLVGSGFKVVVGSRNPKRTARLFPSAAQVTFQEEAVSSP EVIFVAVFREHYSSLCSLSDQLAGKILVDVSNPTEQEHLQHRE SNAEYLASLFPTCTVVKAFNVISAWTLQAGPRDGNRQVPICG DQPEAKRAVSEMALAMGFMPVDMGSLASAWEVEAMPLRL LPAWKVPTLLALGLFVCFYAYNFVRDVLQPYVQESQNKFFK LPVSVVNTTLPCVAYVLLSLVYLPGVLAAALQLRRGTKYQR FPDWLDHWLQHRKQIGLLSFFCAALHALYSFCLPLRRAHRY DLVNLAVKQVLANKSHLWVEEEVWRMEIYLSLGVLALGTL SLLAVTSLPSIANSLNWREFSFVQSSLGFVALVLSTLHTLTYG WTRAFEESRYKFYLPPTFTLTLLVPCVVILAKALFLLPCISRRL ARIRRGWERESTIKFTLPTHDALAEKTSHV |
| 2 | NM_001008410 Human nucleotide | gaggaggagc ctcgggccga gccaccgcct tcgccgcgga ccttcagctg ccgcggtcgct ccgagcggc gggccgcaga gccaccaaaa tgccagaaga gatggacaag ccactgatca gcctccacct ggtggacagc gatagtagcc ttgccaaggt ccccgatgag gcccccaaagt gggcatcct gggtagcggg gactttgccc gctccctggc caracgcctg gtgggctctggcttcaaagt ggtggtgggg agccgcaacc ccaaacgcac agccaggctg tttccctcagcggcccaagt gactttccaa gaggaggcag tgagctcccc ggaggtcatc tttgtggctgtgttccggga gcactactct tcactgtgca gtctcagtga ccagctggcg ggcaagatcctggtggatgC gagcaacccct acagagcaag agcaccttca gcatcgtgag tccaatgctgagtacctggc ctccctcttc cccacttgca cagtggtcaa ggcctttaat gttatctctgcctggaccct gcaggctggc caagggatg gtaacaggca ggtgcccatc tgcggtgaccagccagaagc caagcgtgct gtctcggaga tggcgctcgc catgggcttc atgcccgtgacatcggatc cctggcgtca gcctgggagg tggaggccat gccctgcgc ctcctccggcctggaaggt gcccaccctg ctggccctgg ggctcttcgt ctgcttctat gcctacaacttcgtccggga cgttctgcag ccctatgtgc aggaaagcca gaacaagttc ttcaagctgcccgtgtccgt ggtcaacacc acactgccgt gcgtggccta cgtgctgctg tcactcgtgtacttgcccgg cgtgctggct gctgccctgc agctgcggcg cggcaccaag taccagcgcttccccgactg gctggaccac tggctacagc accgcaagca gatcgggctg ctcagcttcttctgcgccgc cctgcacgcc ctctacagct tctgcttgcc gctgcgccgc gcccaccgctacgacctggt caacctggca gtcaagcagg tcttggccaa caagagccac ctctgggtggaggaggaggt ctggcggatg gagatctacc tctcccttgg agtgctggcc ctcggcacgttgtccctgct ggccgtgacc tcactgccgt ccattgcaaa ctcgctcaac tggagggagttcagcftcgt tcagtcctca ctgggctttg tggccctcgt gctgagcaca ctgcacacgctcacctacgg ctggacccgc gccttcgagg agagccgcta caagagccac ctgcctccaccttcacgct cacgctgctg gtgccctgcg tcgtcatcct ggccaaagcc ctgtttctcctgccctgcat cagccgcaga ctcgccagga tccggagagg ctgggagagg gagagcaccatcaagttcac gctgcccaca gaccacgccc tggccgagaa gacgagccac gtatgaggtgcctgccctgg gctctggacc ccggcacac gagggacggt gccctgagcc cgttaggtttctttttcttg gtggtgcaaa gtggtataac tgtgtgcaaa taggaggttt gaggtccaaattcctgggac tcaaatgtat gcagtactat tcagaatgat atacacacat atgtgtatatgtatttacat atattccaca tatataacag gatttgcaat tatacatagc tagctaaaaagttgggtctc tgagatttca acttgtagat ttaaaaacaa gtgccgtacg ttaagagaaggcagatcat gctattgtga catttgcaga gatatacaca cacttttttgt acagaagaggcttctgctgt ggtgggttcc atttatcctt gcccaccccca cccccacaac ttcccttttgctacttcccc aaggctcng cagacgtagg gctctgaagg ggagggaagg caacggctctgcccagagcc atccctggag catgtgagca gcggctggtc tatccctcc acctggggcagcagraggag gcctggggag gaggaaaatc aggcagtca cctggagtct gtgccaggtcctttgcccgg tggtgggagg atggagggat tgggctgaag ctgctccacc tcatccttgctgagtgggg agcattttc cctgaaagtc agaagtcacc atagagcctg caaatggatcctcctgtgag agtgacgtca cctccttttcc |

TABLE 1-continued

| SEQ ID NO | Accession Number And Description | Amino acid/nucleotide sequence |
|---|---|---|
| | | agagccatta gtgagcctgg cttgggaacaagtgtaattt ccttccctcc tttaacctgg<br>cgatgagcgt ccttttaaacc actgtgccttctcatccttt ccatcttcag tttgaatgac<br>tcccaggaag gcctagagca gacccctttagaaatcagccc aagggggaga<br>gcaagagaaa acactctagg gagtaaaagct ccccgggcgtcagagttgag ccctgcctgg<br>gctgaaggac tgtcttcacg aagtcagtcc tgaggaaaaatattggggac tccaaatgtc<br>ctctggraga ggacccagaa aaccacactg ctccaatttcctcctcatg gggcattaca<br>cttcaaaaca gtggggagca acttttccac caaagctacaaatctaaaat gctgctgccc<br>caaagcacaa gagggaagag caccgccggg gccacaggacgtctgtcctc<br>cagtcacagg ccatccttgc tgctccctac tgactctagc ttacttccctgtgaagaaa<br>cagattgttct cggctgagcc cccaaccctc tgcagaacca ggttgatctgccacagaaaa<br>agcatctttg aagacaaaga gggtgaggtc ttcatgagtc tcctgggcccaaagccatct<br>tctgatggaa ggaagagagt agggccagtg aaggctgccc agagagaatgtcacagatga<br>ggctgcccct gcccccccc cgccagggag gtttcatgag ctcatgtctatgcagcacat<br>aagggacttt cagtgaaaag caggagaaga gccactgca aggatagctcattaggcaca<br>tgaccgatgc agggaaggcc atgccgggga agctcttcct gcaggtattttccatctgct<br>gtgccaaggc tgagcggcag aaacttgtct cataaattgc cactgatggagcatcagctg<br>tggcccacag agagccttgc tgagaagggg gcaggtaaag cagagattttagcattgcct<br>tggcataaca agggcccatc gattccctac taatgagagg caggagagcatgggcaatg<br>gagacccacc aatgatcccc aaccccggtg ggtactggct gcctgccctgggccagggaa<br>tggctcctta taccaaagat gctggcacat agcagaaccc agtgcacgtcctccccttcc<br>cacccacctc tggctgaagg tgctcaagag ggaagcaatt ataaggtgggtggcaggagg<br>gaacagggc cacctgctgg acaatcacac gaaaggcagg cgggctgtgtactgggccct<br>gactgtgcgt ccactgctgt cttccctacc tcaccaggct actggcagcagcatcccgag<br>agcacatcat ctccacagcc tggtaaattc catgtgcctc tgggtacaaaagtgcctcaa<br>cgacatgctc tggaaatccc aaatgccaca gtctgaggtt gatatctaaaatctatgcct<br>tcaaaagagt ctctgttttt tttttttaac ctggtagaca gtataaaagcagtgcaaata<br>aacacctaac cttctgcaaa |
| 3 | NP_001078878<br>Mouse<br>protein | MSGEMDKPLI SRRLVDSDGS LAEVPKEAPK VGILGSGDFA<br>RSLATRLVGS GFSVVVGSRNPKRTAGLFPS LAQVTFQEEA<br>VSSPEVIFVA VFREHYSSLC SLADQLAGKI<br>LVDVSNPTEKEHLQHRQSNA EYLASLFPAC TVVKAFNVIS<br>AWALQAGPRD GNRQVLICSD QPEAKRTISEMARAMGFTPL<br>DMGSLASARE VEAIPLRLLP SWKVPTLLAL GLFVCFYTYN<br>FIRDVLQPIRKDENKFYKM PLSVVNTTLP CVAYVLLSLV<br>YLPGVLAAAL QLRRGTKYQR FPDWLDHWLQHRKQIGLLSF<br>FFAMLHALYS FCLPLRRSHR YDLVNLAVKQ<br>VLANKSRLWA EEEVWRMEIYLSLGVLALGM LSLLAVTSLP<br>SIANSLNWKE FSFVQSTLFG VALILSTMHT<br>LTYGWTRAFEENHYKFYLPP TFTLTLLLPC VILLAKGLFL<br>LPCLNRRLTK IRRGWEKDGA VKFMLPGDHTQGEKTSHV |
| 4 | NM_001085409<br>Mouse<br>nucleotide | tcacactcta tctcagacct tgagctaaag gactctccca aggcgagggg<br>gccactgctt actgggggccc tccacctggg aaggagaggt taaaggtgac ccagggttaa<br>ggagaacctg gtatgccaca tctcaactta tgatgttpgc tccagccacc cagcttcaga<br>agaaatggct gcagaggccc acttggcagca gggctcttgc cccaccatcc cctcagaggg<br>ctgtggaaagt caccagaga agaaaggcag tgcggccgac tctagacctg gtgagctgga<br>gtctgtggggcagggaggaa gcagggcata aagacacag gaagraactc tgccctgatt<br>ccagactccatctgcatgga ctgattccag gtgctagggt tccttttctca gaacccctag<br>aagtccacgaaggcactgct atgtcggggg gatggacaa gccgxtgatc agccgccgcc<br>tagtggacagtgatggcagt ctggctgagg tccccaagga ggccccccaaa gtgggcatcc<br>tgggcagtggggattttgcc cgtttcctgg ccacacgcrt ggtgggctct ggcttcagtg<br>tggtggtgggggagccgtaac cccaaacgca cggctggcct cttcccctcc ttagctcaag<br>tgactttccaggaggaagcc gtgagctctc cagaggtcat ctttgtggcc gtgttcccgg<br>agcactattcctcactgtgc agtctcgctg accagttggc tggcaagatc ctcgtggatg<br>taagcaacccacggagaag gagcatcttc agcaccgcca gtctaacgct gagtacctgg<br>cctcactctttcctgcgtgc actgtggtga aggccttcaa cgtcatctct gcatgggccc<br>tacaggctggcccaagggat gggattcagg cagccagtgt ctgcagtgat cagccagaag<br>Ccaagcgcaccatctcagag atggcacgcg ccatgggttt cacacccctg gacatgggat<br>ccctggcctcagcgaggag gtagaagcca taccctgcg cctccttcca tcctggaagg<br>tgcccaccctcctggcactg gggtcatg tgtgcttcta cacctacaac ttcatccgag<br>acgttctacagccatacatt cggaaagatg agaacaagtt ctacaagatg cccttgtctg<br>tggtcaacaccacactaccc tgtatggctt atgtgctact gtccctagtt tacctgcccg<br>gtgtgctggcagctgcgctt cagctgcgga ggggaccaa gtaccagcgc ttcccagact<br>ggctggaccactggctgcag catcgcaagc agatcgggct gctcagcttc tcttcgcga<br>tgctgcacgctctctacagc ttctgcctgc cgctgcgccg ctcccaccgc tatgatgggg<br>tcatttctggctgtgattgcttg gtcctggcca acaagagccg cttccgggct gaggattgaag<br>tctggaggatggagatatac ctgtccctgg gtgtgtggc cctgggcatg ttgtcgctgc<br>tggctgtcacctcgctcccg tccattgcta attccctcaa ctctgaaggag ttcagcttcg<br>tgcagtccacactgggcttc gtgccctga tactcagcac aatgcacaca ctcactcagg<br>gctggaccegtgcctttgag gaaaaccact acaagttcta cctgccgccc acattcacac<br>tcacgctgctcctgccctgt gtgatcatcc tggccaaggg cctcttcctc ctgccctgcc<br>tcttaccgcagactcttccaag atacgcaggg gctgggagaa agatgggct gtcaagttca<br>tgctgcccggcgaccacaca caggggagaa aaacaagcca cgtgtgaggc<br>cctggaagtg gagatggctt gtgggggccc tgagctgggt tcgggtctct tttctggatg |

TABLE 1-continued

| SEQ ID NO | Accession Number And Description | Amino acid/nucleotide sequence |
|---|---|---|
| | | ctgcacagcg aggtgatgatatatgcgtgg gtggctgaga tcctaattcc tgggatgcag
gtgtaaactg acatactcagaatgacaccc catacatgtg atatgtactt acatatattt
cacatataat aagatttgctattattctta cttagctatta attaaaaaagt gggtccctat
atttcagcgt aagcatttcaaagcaaatgc cacacattga acagcagatc ccacccttgt
ggtatctaca gaggcagacagacactctgg tataggagaa actgtctttc gttggttttct
ctcctttaat ctctatgctccttattagct gaatcctaatt gttggtgcaa agctgggca
agaaatgcct ctggtgccgcctaccccat cccagggcta agaaagaagc ctcgagtgaa
cagggaacca ggtctggactctgctgcttc cctgggcgtg cgtggggagg ctcagcaaga
cccctggaa tctatgcaggagcttttca ggtccgtcct ttcttcaggg aagggtctaa
agctgcccca tctgatcctagctgagctga gaagattctt ccccaccccc tgaaagtcca
gagtcaccac cggagcctgcattattgatcc ttctgcgaag gtgtgattgtc accgcctctc
cagagccatt atttgaacctggtcttcggga ggaggataat tgtttcctct ccattaagtt
gctggtgacc ccccataaatcactgtgc cttctcgcct tttccatcat taatttggac
atctccgtgg agtggacacttgtctgggca gtccggggtg gggggagca ttagagattg
cagagaataa ccatcgaaCcctcttcttgg ggcaaccctc cttttggatg tgcccagc
ctgctttcat taaattggtccctgaggaga ataataggga ccctttttcat ttaccctgtc
tcctgtaggc agaaaacctaccttctgagc acccagaaaa cacagtggcc ccatgctctt
cttcagggg ttccacagcccccttctccg tgtttttgcc tccctctctc cttccttccc
tccctccctc cctcactgttacttttcaacc acaaaagtct tcaaatattg tttttagaa
ttcttaaatt gattctcattttattacaaaa aaaaaaaaaa aa |

The sequence of Steap3 indicates that it is a six-transmembrane protein.

The quantity of Steap3 of the present teachings can be indicated as a value. The value can be one or more numerical values resulting from the evaluation of a sample, and can be derived, e.g., by measuring level(s) of Steap3 in a sample by an assay performed in a laboratory, or from data obtained from a provider such as a laboratory, or from data stored on a server. Steap3 levels can be measured using any of several techniques known in the art, such as those described herein.

The measurement of levels of Steap3 can be determined at the protein or nucleic acid level using any method known in the art. "Protein" detection comprises detection of full-length proteins, mature proteins, pre-proteins, polypeptides, isoforms, mutations, variants, post-translationally modified proteins and variants thereof, and can be detected in any suitable manner. Levels of Steap3 can be determined at the protein level directly or by measuring the enzymatic activities Steap3. Such methods are well-known in the art and include, e.g., immunoassays based on antibodies to proteins encoded by the genes, aptamers or molecular imprints.

Steap3 can also be determined at the nucleic acid level. For example, nucleic acid sequences that correspond Steap3 can be used to construct primers and probes for detecting and/or measuring Steap3 nucleic acids. These probes can be used in, e.g., Northern or Southern blot hybridization analyses, ribonuclease protection assays, and/or methods that quantitatively amplify specific nucleic acid sequences. As another example, Steap3 sequences can be used to construct primers for specifically amplifying Steap3 sequences in, e.g., amplification-based detection and quantitation methods such as reverse-transcription based polymerase chain reaction (RT-PCR) and PCR. When alterations in gene expression are associated with gene amplification, nucleotide deletions, polymorphisms, post-translational modifications and/or mutations, sequence comparisons in test and reference populations can be made by comparing relative amounts of the examined DNA sequences in the test and reference populations.

As an example, Northern hybridization analysis using probes which specifically recognize one or more of these sequences can be used to determine gene expression. Alternatively, expression cart be measured using RT-PCR; e.g., polynucleotide primers specific for the differentially expressed Steap3 mRNA sequences reverse-transcribe the mRNA into DNA, which is then amplified in PCR and can be visualized and quantified. Steap3 RNA can also be quantified using, for example, other target amplification methods, such as TMA, SDA, and NASBA, or signal amplification methods (e.g., bDNA), and the like. Ribonuclease protection assays can also be used, using probes that specifically recognize Steap3 mRNA sequences, to determine gene expression.

In some embodiments, Steap3 is detected by contacting a subject sample with reagents, generating complexes of reagent and analyte, and detecting the complexes. Examples of "reagents" include but are not limited to nucleic acid primers, peptides, small molecules, substrates for the enzyme, and antibodies.

Various methods to detect Steap3 levels are known in the art. For example, various PCR based assays such as TaqMan assays are known in the art and are commercially available. The sequence of Steap3 can be determined using any of the methods for nucleic acid sequence determination known in the art, such as conventional Sanger sequencing or NextGen sequencing methods.

At the protein level, various antibodies directed against the Steap3 protein are known in the art and are commercially available. Steap3 ELISA kits are also commercially available.

Assays to measure Steap3 activity are also known. For example, an assay that measures the production of ferrous iron using 200 μM ferrozinc as an indicator and monitoring the increase in absorbance at λ=562 nm may be used. See, e.g., Ohgami et al., "The Steap proteins are metalloreductases", Blood, 108:1388-1394 (2006).

In some embodiments, data on the level or activity or sequence of Steap3 may be combined with other indicators or biomarkers of blood storage, such as those disclosed in U.S. Patent Application No. 2014/0178904, to obtain a score which is indicative of blood storage quality.

The information from the assays above can be quantitative and sent to a computer system of the invention. The information can also be qualitative, such as observing patterns or fluorescence, which can be translated into a quantitative measure by a user or automatically by a reader or computer system. In an embodiment, the subject can also provide information other than assay information to a computer system, such as race, height, weight, age, gender, eye color, hair color, family medical history and any other information that may be useful to a user, such as a clinical factor described above.

Other embodiments of the present teachings comprise Steap3 detection reagents packaged together in the form of a kit for conducting any of the assays of the present teachings. In certain embodiments, the kits comprise reagents for protein detection of Steap3 proteins, such as antibodies. For example, the kit may comprise antibodies or fragments thereof, specific for Steap3 (primary antibodies), along with one or more secondary antibodies that may incorporate a detectable label; such antibodies may be used in an assay such as an ELISA. Alternately, the antibodies or fragments thereof may be fixed to a solid surface, e.g. an antibody array. In certain embodiments, the kits comprise oligonucleotides that specifically identify one or more Steap3 nucleic acids based on homology and/or complementarity with Steap3 nucleic acids. The oligonucleotide sequences may correspond to fragments of Steap3 nucleic acids. For example, the oligonucleotides can be more than 200, 200, 150, 100, 50, 25, 10, or fewer than 10 nucleotides in length. In other embodiments, the kits comprise antibodies to proteins encoded by the Steap3 nucleic acids. The kits of the present teachings can also comprise aptamers. The kit can contain in separate containers a nucleic acid or antibody (the antibody either bound to a solid matrix, or packaged separately with reagents for binding to a matrix), control formulations (positive and/or negative), and/or a detectable label, such as but not limited to fluorescein, green fluorescent protein, rhodamine, cyanine dyes, Alexa dyes, luciferase, and radiolabels, among others. Instructions for carrying out the assay, including, optionally, instructions for generating a DAI score, can be included in the kit; e.g., written, tape, VCR, or CD-ROM. The assay can for example be in the form of a Northern hybridization or a sandwich ELISA as known in the art.

In some embodiments of the present teachings, Steap3 detection reagents can be immobilized on a solid matrix, such as a porous strip, to form at least one Steap3 detection site. In some embodiments, the measurement or detection region of the porous strip can include a plurality of sites containing a nucleic acid. In some embodiments, the test strip can also contain sites for negative and/or positive controls. Alternatively, control sites can be located on a separate strip from the test strip. Optionally, the different detection sites can contain different amounts of immobilized nucleic acids, e.g., a higher amount in the first detection site and lesser amounts in subsequent sites. Upon the addition of test sample, the number of sites displaying a detectable signal provides a quantitative indication of the amount of Steap3 in the sample. The detection sites can be configured in any suitably detectable shape and can be, e.g., in the shape of a bar or dot spanning the width of a test strip.

In other embodiments of the present teachings, the kit can contain a nucleic acid substrate array comprising one or more nucleic acid sequences. In some embodiments the substrate array can be on a solid substrate, such as what is known as a "chip." See, e.g., U.S. Pat. No. 5,744,305. In some embodiments the substrate array can be a solution array; e.g., xMAP (Luminex, Austin, Tex.), Cyvera (Illumina, San Diego, Calif.), RayBio Antibody Arrays (RayBiotech, Inc., Norcross, Ga.), CellCard (Vitra Bioscience, Mountain View, Calif.) and Quantum Dots' Mosaic (Invitrogen, Carlsbad, Calif.).

In some embodiments, the present invention is practiced using computer implementation. In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The following examples of specific aspects for carrying out the present invention are offered for illustrative purposes only, and are not intended to limit the scope of the present invention in any way.

EXAMPLES

Example 1

Identification of Steap3

Background

There is substantial donor-to-donor variability in the quality of human RBC storage. Like humans, RBCs of different strains of inbred mice store differently; RBCs from C57BL/6 (B6) mice store well whereas RBCs from FVB mice store poorly (24-hr post-transfusion recoveries).

Methods and Materials

B6×FVB F1 mice were interbred to generate an F2 population that has a random assortment of chromosomes, including recombination events. F2 mice were phenotyped by storing RBCS for 7 days, followed by transfusion and calculation of 24 hour recoveries. DNA from each F2 mouse was analyzed using a panel of 1400 single nucleotide polymorphisms (SNPs). Genetic elements associated with RBC post-transfusion survival were identified by Quantitative Trait Loci (QTL) analysis. Additional resolution was obtained by backcrossing F2 mice with poor storage to B6 parents, and selecting poor-storing progeny to breed for each next generation.

Results

QTL analysis of 154 F2 mice revealed a peak signal on chromosome 1 at location rs4137908, with extreme statistical significance (p=2.09E-31). However, the peak was broad, and ranged over 149 Mb (using a false-discovery rate of 0.05). SNP analysis of the backcrossed pedigree was used to further refine the boundaries to a 9.5Mb region, containing 64 genes, 35 of which encoded proteins. Focusing on Non-Synonymous SNPs between B6 and FVB strains identified 5 genes (Gli2, Steap3, Cede93, Rab3gap1, and Tli). Based upon known biology, Steap3 was chosen as a leading candidate. Steap3 is the primary ferrireductase in erythroid cells, converting $Fe^{3+}$ to $Fe^{2+}$, both mitigating oxidative stress and allowing transferrin-dependent iron uptake. Mice lacking Steap3 have profound anemia. Moreover, a human family has been reported with a nonsense mutation in the human steap3 orthologue and a congenital hypochromic anemia. The SNP between B6 and FVB mice leads to an A-V mutation at position 350, which is within the conserved ferric reductase superfamily domain.

Example 2

Steap3 Activity and RBC Storage

Figure 1B:
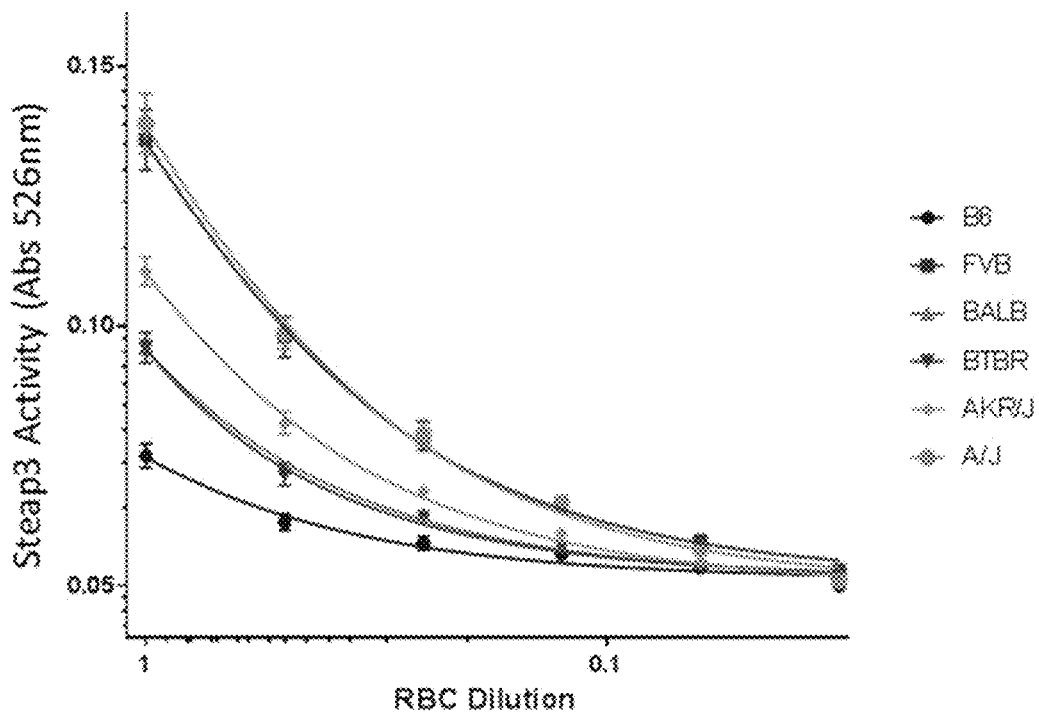
Figure 1C:
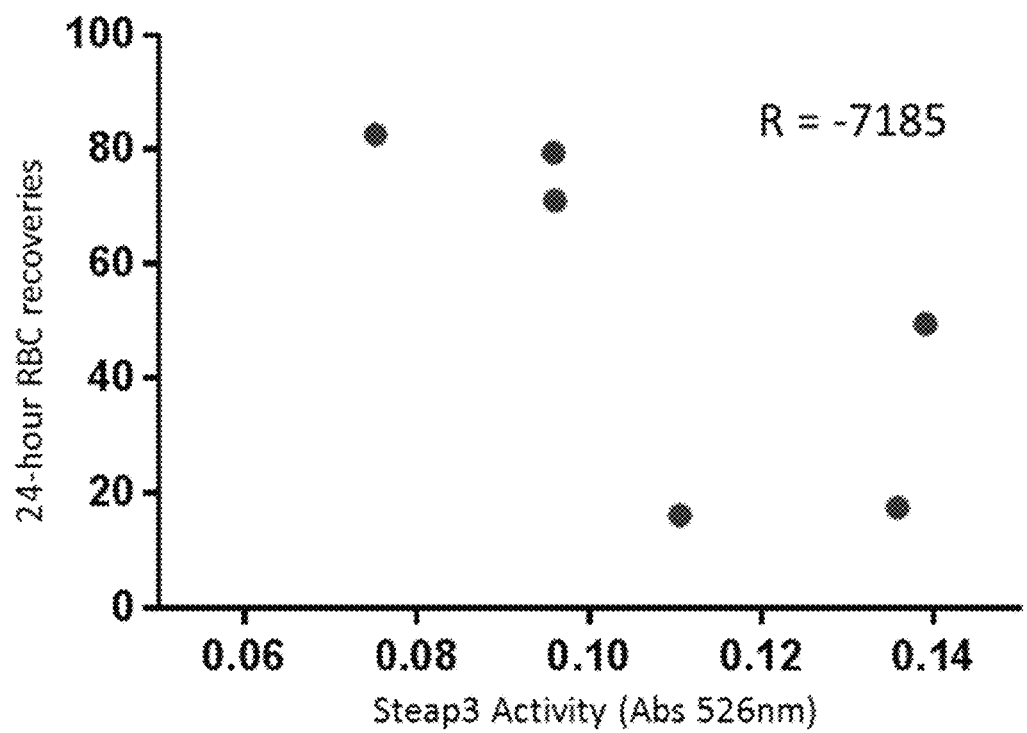

To test the ability of measuring Steap3 activity as a predictor of RBC storage from genetically distinct donors, in a pre-clinical tractable animal model, a variety of different strains of mice was characterized for RBC storage properties. Each strain had slightly different RBC storage characteristics, as measured by post-transfusion 24-hour recoveries of stored RBCs (FIG. 1A). 6 particular strains, ranging in storage, were chosen for further analysis by ferrozine assay (measuring Steap3 activity)—(see FIG. 1B). A Pearson's correlation coefficient of −0.7185 was observed between the ferrozine activity and the 24-hr RBC recoveries (FIG. 1C). These data demonstrate, in a whole animal model, that measuring Steap3 activity predicts (as an inverse relationship) the post-transfusion circulation of RBCs (e.g. 24-hour recovery) for donors of different genetic composition.

REFERENCES 1. van de Watering L. Red cell storage and prognosis. Vox Sang 2011; 100: 36-45.
2. van de Watering L. Pitfalls in the current published observational literature on the effects of red blood cell storage. Transfusion 2011; 51: 1847-1854.
3. Fergusson D A, Hebert P, Hogan D L, LeBel L, Rouvinez-Bouali N, Smyth J A, Sankaran K, Tinmouth A, Blajchman M A, Kovacs L, Lachance C, Lee S, Walker C R, Hutton B, Ducharme R, Balchin K, Ramsay T, Ford J C, Kakadekar A, Ramesh K, Shapiro S. Effect of fresh red blood cell transfusions on clinical outcomes in premature, very low-birth-weight infants: the ARIPI randomized trial. JAMA 2012; 308: 1443-1451.
4. Lacroix J, Hebert P, Fergusson D, Tinmouth A, Blajchman M A, Callum J, Cook D, Marshall J C, McIntyre L, Turgeon A F. The Age of Blood Evaluation (ABLE) randomized controlled trial: study design. Transfus Med Rev 2011; 25: 197-205.
5. Steiner M E, Assmann S F, Levy J H, Marshall J, Pulkrabek S, Sloan S R, Triulzi D, Stowell C P. Addressing the question of the effect of RBC storage on clinical outcomes: the Red Cell Storage Duration Study (RECESS) (Section 7). Transfus Apher Sci 2010; 43: 107-116.
6. Hess J R. Red cell changes during storage. Transfus Apher Sci 2010; 43: 51-59.
7. Hess J R. Red cell storage. J Proteomics 2010; 73: 368-373.
8. Hod E A, Brittenham G M, Billote G B, Francis R O, Ginzburg Y Z, Hendrickson J E, Jhang J, Schwartz J, Sharma S, Sheth S, Sircci A N, Stephens H L, Stotler B A, Wojczyk B S, Zimring J C, Spitalnik S L. Transfusion of human volunteers with older, stored red blood cells produces extravascular hemolysis and circulating non-transferrin-bound iron. Blood 2011; 118: 6675-6682.
9. Hod E A, Spitalnik S L. Harmful effects of transfusion of older stored red blood cells: iron and inflammation. Transfusion 2011; 51: 881-885.
10. Hod E A, Spitalnik S L. Stored red blood cell transfusions: Iron, inflammation, immunity, and infection. Transfus Clin Biol 2012; 19: 84-89.
11. Hod E A, Zhang N, Sokol S A, Wojczyk B S, Francis R O, Ansaldi D, Francis K P, Della-Latta P, Whittier S, Sheth S, Hendrickson J E, Zimring J C, Brittenham G M, Spitalnik S L. Transfusion of red blood cells after prolonged storage produces harmful effects that are mediated by iron and inflammation. Blood 2010; 115: 4284-4292.
12. Kor D J, Van Buskirk C M, Gajic O. Red blood cell storage lesion. Bosn J Basic Med Sci 2009; 9 Suppl 1: 21-27.
13. Silliman C C, Moore E E, Kelher M R, Khan S Y, Gellar L, Elzi D J. Identification of lipids that accumulate during the routine storage of prestorage leukoreduced red blood cells and cause acute lung injury. Transfusion 2011; 51: 2549-2554.
14. Tissot J D, Rubin O, Canellini G. Analysis and clinical relevance of microparticies from red blood cells. Curr Opin Hematol 2010; 17: 571-577.
15. Dumont L J, AuBuchon J P. Evaluation of proposed FDA criteria for the evaluation of radiolabeled red cell recovery trials. Transfusion 2008; 48: 1053-1060.
16. Gilson C R, Kraus T S, Hod E A, Hendrickson J E, Spitalnik S L, Hillyer C D, Shaz B H, Zimring J C. A novel mouse model of red blood cell storage and post-transfusion in vivo survival. Transfusion 2009; 49: 1546-1553.

While specific aspects of the invention have been described and illustrated, such aspects should be considered illustrative of the invention only and not as limiting the invention as construed in accordance with the accompanying claims.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed:

1. A method of testing and determining the suitability of a donor red blood cell (RBC) unit for administration to a subject in need of a transfusion, the method comprising:

a) obtaining a test RBC sample from an RBC unit obtained from a donor;

b) obtaining a control RBC sample from a control RBC unit that is suitable for transfusion;

c) assaying and measuring the level of Steap3 ferric reductase activity in each of the test RBC sample and the control RBC sample d) comparing the measured level of Steap3 ferric reductase activity in the test RBC sample with the measured level of Steap3 ferric reductase activity in the control RBC sample; and e) determining that the donor RBC unit is suitable for transfusion when the measured level of Steap3 ferric reductase activity in the test RBC sample is lower relative to the corresponding measured level in the control RBC sample, or f) determining that the donor RBC unit is not suitable for transfusion when the measured level of Steap3 ferric reductase activity in the test RBC sample is higher relative to the corresponding measured level in the control RBC sample; and g) releasing and administering the donor RBC unit to the subject in need of the transfusion when step e) is indicated.

2. The method of claim 1, wherein the assaying and measuring is performed at the time of collection of the test RBC sample.

3. The method of claim 1, wherein the assaying and measuring is performed during the time of storage of the test RBC sample.

4. The method of claim 1, wherein the measured level of Steap3 ferric reductase activity in the test RBC sample is 2-200 fold higher relative to the corresponding measured level in the control RBC sample.

5. The method of claim 1, wherein the assaying and measuring the level of Steap3 ferric reductase activity further comprises:
   measuring the production of ferrous iron using ferrozine as an indicator; and
   monitoring increase in absorbance of ferrous iron-ferrozine complex at $\lambda=562$ nm.

6. The method of claim 5, wherein the ferrozine is at 200 μM.

7. A method of testing and determining the suitability of a donor red blood cell (RBC) unit for transfusion to a subject in need thereof, the method comprising:
   a) obtaining a test RBC sample from an RBC unit obtained from a donor;
   b) obtaining a control RBC sample from a control RBC unit that is suitable for transfusion;
   c) assaying and measuring the level of Steap3 ferric reductase activity in each of the test RBC sample and the control RBC sample;
   d) comparing the measured level of Steap3 ferric reductase activity in the test RBC sample with the measured level of Steap3 ferric reductase activity in the control RBC sample; and
   e) determining that the donor RBC unit is suitable for transfusion when the measured level of Steap3 ferric reductase activity in the test RBC sample is lower relative to the corresponding measured level in the control RBC sample, or f) determining that the donor RBC unit is not suitable for transfusion when the measured level of Steap3 ferric reductase activity in the test RBC sample is higher relative to the corresponding measured level in the control RBC sample; and
   g) releasing and transfusing the donor RBC unit into the subject in need thereof when step e) is indicated.

8. The method of claim 7, wherein the assaying and measuring is performed at the time of collection of the test RBC sample.

9. The method of claim 7, wherein the assaying and measuring is performed during the time of storage of the test RBC sample.

10. The method of claim 7, wherein the measured level of Steap3 ferric reductase activity in the test RBC sample is 2-200 fold higher relative to the corresponding measured level in the control RBC sample.

11. The method of claim 7, wherein the assaying and measuring the level of Steap3 ferric reductase activity further comprises:
   measuring the production of ferrous iron using ferrozine as an indicator; and
   monitoring increase in absorbance of ferrous iron-ferrozine complex at $\lambda=562$ nm.

12. The method of claim 11, wherein the ferrozine is at 200 μM.

* * * * *